United States Patent
Fischer et al.

(10) Patent No.: US 8,623,904 B2
(45) Date of Patent: Jan. 7, 2014

(54) USE OF TETRAMIC ACID DERIVATIVES FOR CONTROLLING PESTS BY WATERING OR DROPLET APPLICATION

(75) Inventors: Reiner Fischer, Monheim (DE); Dirk Ebbinghaus, Wuppertal (DE); Jürgen Kühnhold, Bergisch Gladbach (DE); Wolfgang Thielert, Odenthal (DE); Yumi Hattori, Yuki (JP); Haruko Sawada, Yuki (JP)

(73) Assignee: Bayer CropScience AG, Monheim (DE)

( * ) Notice: Subject to any disclaimer, the term of this patent is extended or adjusted under 35 U.S.C. 154(b) by 472 days.

(21) Appl. No.: 12/810,000

(22) PCT Filed: Dec. 16, 2008

(86) PCT No.: PCT/EP2008/010680
§ 371 (c)(1),
(2), (4) Date: Jun. 21, 2010

(87) PCT Pub. No.: WO2009/083132
PCT Pub. Date: Jul. 9, 2009

(65) Prior Publication Data
US 2010/0267797 A1    Oct. 21, 2010

(30) Foreign Application Priority Data
Dec. 21, 2007    (EP) .................... 07150293

(51) Int. Cl.
*A01N 43/38*    (2006.01)
*A01P 3/00*    (2006.01)

(52) U.S. Cl.
USPC .......................... 514/409; 424/404

(58) Field of Classification Search
USPC .......................... 514/409; 424/404
See application file for complete search history.

(56) References Cited

U.S. PATENT DOCUMENTS

| | | |
|---|---|---|
| 6,114,374 A | 9/2000 | Lieb et al. |
| 2005/0032885 A1 | 2/2005 | Fischer et al. |
| 2007/0032539 A1 | 2/2007 | Himmler |
| 2007/0275858 A1 | 11/2007 | Fischer et al. |
| 2009/0099247 A1 | 4/2009 | Macom et al. |
| 2009/0298903 A1 | 12/2009 | Fischer et al. |
| 2009/0306147 A1 | 12/2009 | Marczok et al. |
| 2010/0099717 A1 | 4/2010 | Vermeer et al. |
| 2010/0313310 A1 | 12/2010 | Andersch et al. |
| 2010/0324303 A1 | 12/2010 | Fischer |

FOREIGN PATENT DOCUMENTS

| | | |
|---|---|---|
| DE | 102 39 479 A1 | 3/2004 |
| WO | WO 98/05638 A2 | 2/1998 |
| WO | WO 03/029213 A1 | 4/2003 |
| WO | WO 2004/007448 A1 | 1/2004 |
| WO | WO 2007/126691 A2 | 11/2007 |
| WO | WO 2008/037373 A2 | 4/2008 |
| WO | WO 2008/037379 A1 | 4/2008 |

OTHER PUBLICATIONS

International Search Report for International Application No. PCT/EP2008/010680, European Patent Office, Rijswijk, Netherlands, mailed on Jul. 7, 2009.

*Primary Examiner* — Kortney L Klinkel
(74) *Attorney, Agent, or Firm* — Sterne, Kessler, Goldstein & Fox P.L.L.C.

(57) ABSTRACT

Compounds of the formulae (I) and (II)

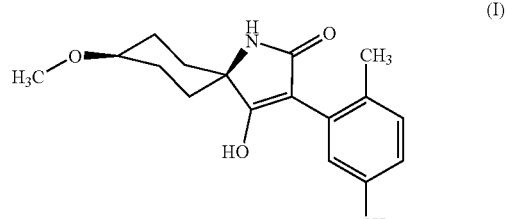

(I)

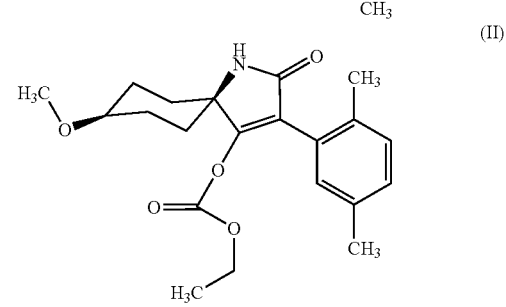

(II)

for controlling pathogens by drenching or drip application.

10 Claims, No Drawings

USE OF TETRAMIC ACID DERIVATIVES FOR CONTROLLING PESTS BY WATERING OR DROPLET APPLICATION

The present invention relates to the use of tetramic acid derivatives for controlling pathogens by drenching or drip application.

Tetramic acid derivatives (WO 98/05638) and also their cis isomers (WO 04/007448) having insecticidal and/or acaricidal activity are known.

Also known is the use of tetramic acid derivatives against spider mites and insects after drenching, drip application or soil injection (WO 07/126,691).

Moreover, a fungicidal action of biphenyl-substituted tetramic acid derivatives following foliar application has been disclosed in WO 03/059065.

Surprisingly, it has now been found that the compounds of the formulae (I) and (II)

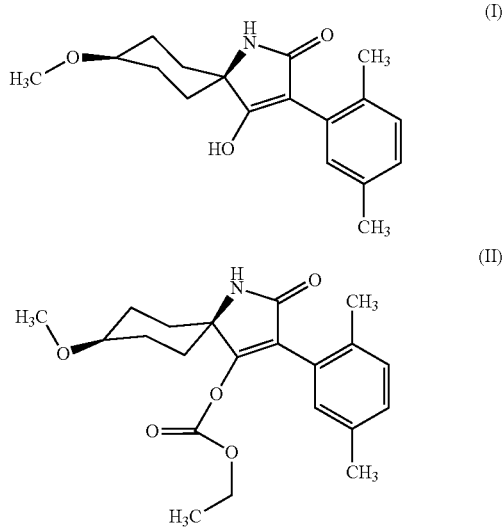

are likewise suitable for controlling pathogens by drenching or drip application.

Emphasis is given to compounds of the formula (I).

Emphasis is also given to compounds of the formula (II).

Accordingly, the present invention relates to the use of tetramic acid derivatives for controlling pathogens by drenching or in irrigation systems as drip application. The present invention furthermore relates to these application forms on natural substrates (soil) or artificial substrates (for example rock wool, glass wool, quartz sand, gravel, expanded clay, vermiculite), outdoors or in closed systems (for example greenhouses or under cloches) and in annual (for example vegetables, spices, ornamental plants) crops.

The crops to be protected which have only been described in general terms will be described in greater detail and specified hereinbelow. Thus, as regards the use, vegetables are understood as meaning for example fruiting vegetables and inflorescences as vegetables, for example bell peppers, chilies, tomatoes, aubergines, cucumbers, pumpkins, courgettes, broad beans, runner beans, dwarf beans, peas, artichokes, corn;

but also leafy vegetables, for example head-forming lettuce, chicory, endives, various types of cress, of rocket, lamb's lettuce, iceberg lettuce, leeks, spinach, Swiss chard;

furthermore tuber vegetables, root vegetables and stem vegetables, for example celeriac/celery, beetroot, carrots, radish, horseradish, scorzonera, asparagus, beet for human consumption, palm hearts, bamboo shoots, furthermore bulb vegetables, for example onions, leeks, Florence fennel, garlic;

furthermore *Brassica* vegetables such as cauliflower, broccoli, kohlrabi, red cabbage, white cabbage, curly kale, Savoy cabbage, Brussels sprouts, Chinese cabbage.

As regards the use, ornamentals are understood as meaning annual and perennial plants, for example cut flowers such as, for example, roses, carnations, gerbera, lilies, marguerites, chrysanthemums, tulips, narcissi, anemones, poppies, amaryllis, dahlias, azaleas, hibiscus, but also for example bedding plants, pot plants and perennials such as, for example, roses, Tagetes, violas, geraniums, fuchsias, hibiscus, chrysanthemums, busy lizzies, cyclamen, African violet, sunflowers, begonias, As regards the use, spices are understood as meaning annual and perennial plants such as, for example, aniseed, chili pepper, paprika, pepper, vanilla, marjoram, thyme, cloves, juniper berries, cinnamon, tarragon, coriander, saffron, ginger.

Fungicides are employed in crop protection for controlling Plasmodiophoromycetes, Oomycetes, Chytridiomycetes, Zygomycetes, Ascomycetes, Basidiomycetes and Deuteromycetes.

Bactericides can be employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above may be mentioned as examples, but not by way of limitation:

Fungicides are employed in crop protection for controlling Plasmodiophoromycetes, Oomycetes, Chytridiomycetes, Zygomycetes, Ascomycetes, Basidiomycetes and Deuteromycetes.

Bactericides can be employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above may be mentioned as examples, but not by way of limitation:

diseases caused by powdery mildew pathogens, such as, for example,

*Blumeria* species, such as, for example, *Blumeria graminis;*

*Leveillula* species, such as, for example, *Leveillula taurica;*

*Oidium* species, such as, for example, *Oidium lycopersicum;*

*Podosphaera* species, such as, for example, *Podosphaera leucotricha;*

*Sphaerotheca* species, such as, for example, *Sphaerotheca fuliginea;*

*Uncinula* species, such as, for example, *Uncinula necator;* diseases caused by rust disease pathogens, such as, for example,

*Gymnosporangium* species, such as, for example, *Gymnosporangium sabinae:*

*Hemileia* species, such as, for example, *Hemileia vastatrix;*

*Phakopsora* species, such as, for example, *Phakopsora pachyrhizi* and *Phakopsora meibomiae;*

*Puccinia* species, such as, for example, *Puccinia recondita;*

*Uromyces* species, such as, for example, *Uromyces appendiculatus;* diseases caused by pathogens from the group of the Oomycetes, such as, for example,

*Bremia* species, such as, for example, *Bremia lactucae*;
*Peronospora* species, such as, for example, *Peronospora pisi* or *P. brassicae*;
*Phytophthora* species, such as, for example, *Phytophthora infestans*;
*Plasmopara* species, such as, for example, *Plasmopara viticola*;
*Pseudoperonospora* species, such as, for example, *Pseudoperonospora humuli* or *Pseudoperonospora cubensis*;
*Pythium* species, such as, for example, *Pythium ultimum*;
leaf blotch diseases and leaf wilt diseases caused, for example, by
*Alternaria* species, such as, for example, *Alternaria solani*;
*Cercospora* species, such as, for example, *Cercospora beticola*;
*Cladosporium* species, such as, for example, *Cladosporium cucumerinum*;
*Cochliobolus* species, such as, for example, *Cochliobolus sativus*
(conidia form: Drechslera, syn: *Helminthosporium*);
*Colletotrichum* species, such as, for example, *Colletotrichum lindemuthanium*;
*Cycloconium* species, such as, for example, *Cycloconium oleaginum*;
*Diaporthe* species, such as, for example, *Diaporthe citri*;
*Elsinoe* species, such as, for example, *Elsinoe fawcettii*;
*Gloeosporium* species, such as, for example, *Gloeosporium laeticolor*;
*Glomerella* species, such as, for example, *Glomerella cingulata*;
*Guignardia* species, such as, for example, *Guignardia bidwelli*;
*Leptosphaeria* species, such as, for example, *Leptosphaeria maculans*;
*Magnaporthe* species, such as, for example, *Magnaporthe grisea*;
*Mycosphaerella* species, such as, for example, *Mycosphaerella graminicola* and *Mycosphaerella fijiensis*;
*Phaeosphaeria* species, such as, for example, *Phaeosphaeria nodorum*;
*Pyrenophora* species, such as, for example, *Pyrenophora teres*;
*Ramularia* species, such as, for example, *Ramularia collocygni*;
*Rhynchosporium* species, such as, for example, *Rhynchosporium secalis*;
*Septoria* species, such as, for example, *Septoria apii*;
*Typhula* species, such as, for example, *Typhula incarnata*;
*Venturia* species, such as, for example, *Venturia inaequalis*;
root and stem diseases caused, for example, by
*Corticium* species, such as, for example, *Corticium graminearum*;
*Fusarium* species, such as, for example, *Fusarium oxysporum*;
*Gaeumannomyces* species, such as, for example, *Gaeumannomyces graminis*;
*Rhizoctonia* species, such as, for example, *Rhizoctonia solani*;
*Tapesia* species, such as, for example, *Tapesia acuformis*;
*Thielaviopsis* species, such as, for example, *Thielaviopsis basicola*;
ear and panicle diseases (including corn cobs) caused, for example, by
*Alternaria* species, such as, for example, *Alternaria* spp.;
*Aspergillus* species, such as, for example, *Aspergillus flavus*;
*Cladosporium* species, such as, for example, *Cladosporium cladosporioides*;
*Claviceps* species, such as, for example, *Claviceps purpurea*;
*Fusarium* species, such as, for example, *Fusarium culmorum*;
*Gibberella* species, such as, for example, *Gibberella zeae*;
*Monographella* species, such as, for example, *Monographella nivalis*;
diseases caused by smut fungi, such as, for example,
*Sphacelotheca* species, such as, for example, *Sphacelotheca reiliana*;
*Tilletia* species, such as, for example, *Tilletia caries*;
*Urocystis* species, such as, for example, *Urocystis occulta*;
*Ustilago* species, such as, for example, *Ustilago nuda*;
fruit rot caused, for example, by
*Aspergillus* species, such as, for example, *Aspergillus flavus*;
*Botrytis* species, such as, for example, *Botrytis cinerea*;
*Penicillium* species, such as, for example, *Penicillium expansum* and *Penicillium purpurogenum*;
*Sclerotinia* species, such as, for example, *Sclerotinia sclerotiorum*;
*Verticilium* species, such as, for example, *Verticilium alboatrum*;
seed- and soil-borne rot and wilt diseases, and also diseases of seedlings, caused, for example, by
*Alternaria* species, such as, for example, *Alternaria brassicicola*;
*Aphanomyces* species, such as, for example, *Aphanomyces euteiches*;
*Ascochyta* species, such as, for example, *Ascochyta lentis*;
*Aspergillus* species, such as, for example, *Aspergillus flavus*;
*Cladosporium* species, such as, for example, *Cladosporium herbarum*;
*Cochliobolus* species, such as, for example, *Cochliobolus sativus*;
(conidia form: Drechslera, Bipolaris Syn: *Helminthosporium*);
*Colletotrichum* species, such as, for example, *Colletotrichum coccodes*;
*Fusarium* species, such as, for example, *Fusarium culmorum*;
*Gibberella* species, such as, for example, *Gibberella zeae*;
*Macrophomina* species, such as, for example, *Macrophomina phaseolina*;
*Monographella* species, such as, for example, *Monographella nivalis*;
*Penicillium* species, such as, for example, *Penicillium expansum*;
*Phoma* species, such as, for example, *Phoma lingam*;
*Phomopsis* species, such as, for example, *Phomopsis sojae*;
*Phytophthora* species, such as, for example, *Phytophthora cactorum*;
*Pyrenophora* species, such as, for example, *Pyrenophora graminea*;
*Pyricularia* species, such as, for example, *Pyricularia oryzae*;
*Pythium* species, such as, for example, *Pythium ultimum*;
*Rhizoctonia* species, such as, for example, *Rhizoctonia solani*;
*Rhizopus* species, such as, for example, *Rhizopus oryzae*

*Sclerotium* species, such as, for example, *Sclerotium rolfsii;*

*Septoria* species, such as, for example, *Septoria nodorum;*

*Typhula* species, such as, for example, *Typhula incarnata;*

*Verticillium* species, such as, for example, *Verticillium dahliae* cancerous diseases, galls and witches' broom caused, for example, by

*Nectria* species, such as, for example, *Nectria galligena;* wilt diseases caused, for example, by

*Monilinia* species, such as, for example, *Monilinia laxa;* deformations of leaves, flowers and fruits caused, for example, by

*Taphrina* species, such as, for example, *Taphrina deformans;* degenerative diseases of woody plants caused, for example, by

*Esca* species, such as, for example, *Phaeomoniella chlamydospora* and *Phaeoacremonium aleophilum* and *Fomitiporia mediterranea;* diseases of flowers and seeds caused, for example, by

*Botrytis* species, such as, for example, *Botrytis cinerea;* diseases of plant tubers caused, for example, by

*Rhizoctonia* species, such as, for example, *Rhizoctonia solani;*

*Helminthosporium* species, such as, for example, *Helminthosporium solani;* diseases caused by bacterial pathogens, such as, for example,

*Xanthomonas* species, such as, for example, *Xanthomonas campestris* pv. *oryzae;*

*Pseudomonas* species, such as, for example, *Pseudomonas syringae* pv. *lachrymans;*

*Erwinia* species, such as, for example, *Erwinia amylovora.*

Emphasis is given to the control of powdery mildew pathogens.

Emphasis is also given to the control of rust disease pathogens.

The invention is illustrated by the examples below. However, the invention is not limited to the examples.

EXAMPLE 1

8 plots each 2.25 m² in size with bell pepper plants of the cultivar "Shishitou aoi" are, in two replications, watered with 50 ml of an active compound solution comprising the active compound (II) (formulation: 240 SC) at the stated application rate. Following a severe natural infection with *Leveillula taurica*, evaluation is carried out 21 days after the treatment by determining the efficacy using the Abbott formula*.

TABLE A

| Active compound (II) | |
| --- | --- |
| Application rate (mg of active compound/ plant) | Efficacy (% Abbott) against *Leveillula taurica* 21 d |
| 40 | 87.4 |
| 60 | 100 |
| 80 | 100 |

EXAMPLE 2

In each case three tomato plants of the cultivar "Hoffmanns Rendita" on rock wool are, in two replications, watered one week after transplantation with in each case 100 ml of active compound solution comprising the active compound (II) (formulation: 240 SC) at the stated application rate. The greenhouse temperature is 20° C. during the day and 17° C. at night. Infection with the powdery mildew *Oidium Iycopersicum* is in each case carried out two and seven days after the active compound application. Evaluation is in each case carried out 14, 23, 28, 35 days after the respective infection by determining the efficacy on the old leaves and the new growth using the Abbott formula*.

TABLE B

| Active compound (II) | | | | |
| --- | --- | --- | --- | --- |
| Application rate (mg of active compound/ plant) | Efficacy (% Abbott) against *Oidium Iycopersicum* | | | |
| | 14 d | 23 d | 28 d old leaves | 28 d new growth |
| 40 2 d prior to infection | 33 | 40 | 41 | 65 |
| 40 7 d prior to infection | 45 | 45 | 45 | 77 |

Calculation of the efficacy according to Abbott:

$$\text{efficacy } (\%) = \frac{(X-Y)}{X \times 100}$$

where X=value for the control and Y=value for the compound tested

The invention claimed is:

1. A method for controlling powdery mildew on a plant infested with powdery mildew comprising applying to the plant an active compound of the formulae (I) or (II)

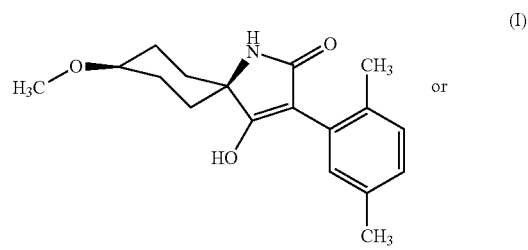

(I)

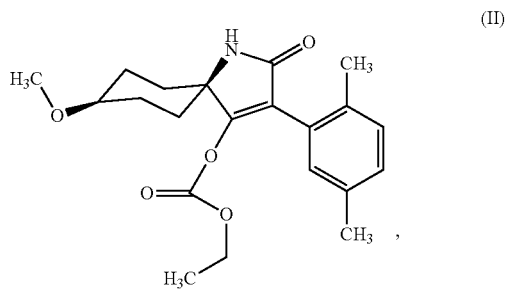

(II)

wherein said applying is by drenching or drip application.

2. The method of claim 1, wherein the plant is grown in an artificial growth substrate.

3. The method of claim 2, wherein the artificial growth substrate is selected from the group consisting of rock wool, glass wool, quartz sand, gravel, expanded clay and vermiculite.

4. The method of claim 1, wherein the plant is planted in a closed system.

5. The method of claim 1, wherein the plant is selected from the group consisting of vegetables, spices and ornamental plants.

6. The method of claim 4, wherein the plant is a vegetable.

7. The method of claim 1, wherein the contacting with the active compound is by drenching.

8. The method of claim 1, wherein the contacting with the active compound is by drip application.

9. The method of claim 1, wherein the powdery mildew are from the *Leveillula* species.

10. The method of claim 1, wherein the powdery mildew are from the *Oidium* species.

* * * * *